United States Patent [19]
Zamponi et al.

[11] Patent Number: 6,011,140
[45] Date of Patent: Jan. 4, 2000

[54] REACTIVE AZO DYES WITH AN AMINONAPHTHALENESULFONIC ACID COUPLING COMPONENT AND INTERMEDIATES THEREFOR

[75] Inventors: Andrea Zamponi, Heidelberg; Manfred Patsch, Wachenheim; Hermann Löffler, Speyer, all of Germany

[73] Assignee: BASF Aktiengesellschaft, Ludwigshafen, Germany

[21] Appl. No.: 09/101,183

[22] PCT Filed: Jan. 3, 1997

[86] PCT No.: PCT/EP97/00013

§ 371 Date: Jul. 6, 1998

§ 102(e) Date: Jul. 6, 1998

[87] PCT Pub. No.: WO97/25377

PCT Pub. Date: Jul. 17, 1997

[30] Foreign Application Priority Data

Jan. 11, 1996 [DE] Germany ............... 196 00 765

[51] Int. Cl.$^7$ ............ C09B 62/08; C09B 62/507; D06P 1/38
[52] U.S. Cl. ............ 534/637; 534/642; 562/43; 562/44; 8/549
[58] Field of Search ............ 534/637, 642; 562/43, 44

[56] References Cited

U.S. PATENT DOCUMENTS

| | | | |
|---|---|---|---|
| 2,824,865 | 2/1958 | Weber et al. | 534/702 |
| 5,023,326 | 6/1991 | Tzikas et al. | 534/638 |
| 5,545,236 | 8/1996 | Hihara et al. | 8/549 |
| 5,625,089 | 4/1997 | Patsch | 558/26 |
| 5,789,557 | 8/1998 | Dornhagen et al. | 534/642 X |

FOREIGN PATENT DOCUMENTS

| | | |
|---|---|---|
| 2199871 | 4/1996 | Canada . |
| 0 369 385 | 5/1990 | European Pat. Off. . |
| 0 637 615 | 2/1995 | European Pat. Off. . |
| 44 34 989 | 4/1996 | Germany . |
| 195 08 311 | 9/1996 | Germany . |
| 96/10610 | 4/1996 | WIPO . |

OTHER PUBLICATIONS

Ames et al., Chemical Abstracts, 53:5608f, 1959.
Majerova et al., Chemical Abstracts, 78:125823n, 1973.
Hegar, Chemical Abstracts, 80:72064y, 1974.

*Primary Examiner*—Fiona T. Powers
*Attorney, Agent, or Firm*—Oblon, Spivak, McClelland, Maier & Neustadt, P.C.

[57] ABSTRACT

Reactive dyes of the formula

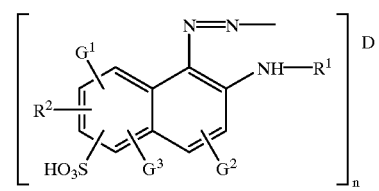

where n is 1 or 2, $G^1$ is hydrogen or hydroxyl, $G^2$ is hydrogen or hydroxysulfonyl, $G^3$ is hydrogen or arylazo, $R^1$ is hydrogen or hydroxysulfonylmethyl, $R^2$ is hydrogen or hydroxysulfonylmethyl, and D is the radical of a diazo or tetraazo component having in each case at least one anchor radical of the formula $SO_2$—Y, where Y is vinyl or substituted ethyl, their use for dyeing or printing hydroxyl-containing or nitrogenous organic substrates, and naphthylamines as intermediates therefor.

11 Claims, No Drawings

REACTIVE AZO DYES WITH AN AMINONAPHTHALENESULFONIC ACID COUPLING COMPONENT AND INTERMEDIATES THEREFOR

This application is a 371 of PCT/EP97/00013 filed Jan. 3, 1997.

The present invention relates to novel reactive dyes of the formula I

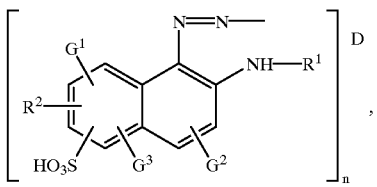

(I)

where n is 1 or 2, $G^1$ is hydrogen or hydroxyl, $G^2$ is hydrogen or hydroxysulfonyl, $G^3$ is hydrogen or a radical of the formula

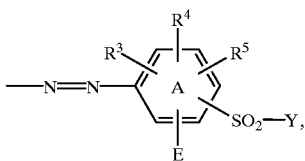

$R^1$ is hydrogen or hydroxysulfonylmethyl, $R^2$ is hydrogen or hydroxyfonlymethyl, and D is, when n is 1, a radical of the formula

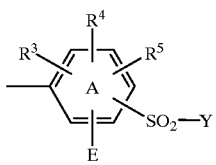

or, when n is 2, a radical of the formula

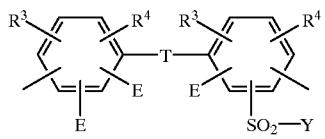

where the ring A may be benzofused, $R^3$, $R^4$ and $R^5$ are each independently of the others hydrogen, $C_1$–$C_4$-alkyl, $C_1$–$C_4$-alkoxy, halogen or hydroxysulfonyl, E is hydrogen, a heterocyclic anchor radical or a anchor radical of the aliphatic series, Y is vinyl or a radical of the formula $C_2H_4$—Q, where Q is an alkali-detachable group, and T is a bridge member, with the proviso that at least one hydroxysulfonylmethyl group shall be present in the molecule and that dyes of the formula

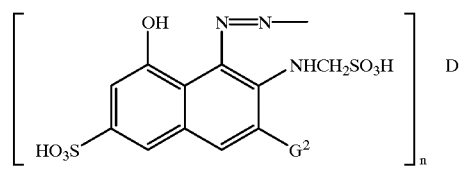

where n, D and $G^2$ are each as defined above, shall be excluded, to their use for dyeing or printing hydroxyl-containing or nitrogenous organic substrates and to naphthylamines as intermediates therefor.

The above-excluded dyes and intermediates are known from prior patent application WO 9610610.

It is an object of the present invention to provide novel reactive dyes derived from phenyl- or naphthalene-azo-naphthalene dyes. The novel dyes shall have an advantageous application property profile.

We have found that this object is achieved by the reactive dyes of the formula I defined at the beginning.

The novel reactive dyes of the formula I are each indicated in the form of the free acid, but salts thereof are also encompassed by the claims, of course.

Suitable cations are derived from metal or ammonium ions. Metal ions are in particular the lithium, sodium or potassium ions. Ammonium ions for the purposes of the present invention are substituted or unsubstituted ammonium cations. Substituted ammonium cations include for example monoalkyl-, dialkyl-, trialkyl-, tetraalkyl- or benzyltrialkyl-ammonium cations or cations derived from nitrogenous five- or six-membered saturated heterocycles, such as pyrrolidinium, piperidinium, morpholinium or piperazinium cations or their N-monoalkyl- or N,N-dialkyl-substituted products. Alkyl is generally to be understood as meaning straight-chain or branched $C_1$–$C_{20}$-alkyl which may be substituted by 1 or 2 hydroxyl groups and/or interrupted by from 1 to 4 oxygen atoms in ether function.

Any alkyl or alkylene herein can be straight-chain or branched.

Any substituted alkyl herein generally contains 1 or 2 substituents.

Any substituted phenylene herein contains for example, unless otherwise stated, $C_1$–$C_4$-alkyl, $C_1$–$C_4$-alkoxy, halogen, hydroxysulfonyl, sulfamoyl or mono- or di-$C_1$–$C_4$-alkylsulfamoyl as substituents. Substituted phenylene then generally contains from 1 to 3, preferably 1 or 2, substituents.

$R^3$, $R^4$ and $R^5$ are each for example methyl, ethyl, propyl, isopropyl, butyl, isobutyl, sec-butyl, tert-butyl, methoxy, ethoxy, propoxy, isopropoxy, butoxy, isobutoxy, sec-butoxy, fluorine, chlorine or bromine.

Q is an alkali-detachable group. Such groups include for example chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, substituted or unsubstituted phenylsulfonyloxy, $C_1$–$C_4$-alkanoyloxy, $C_1$–$C_4$-dialkylamino or a radical of the formula

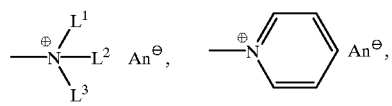

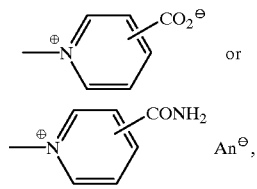

where $L^1$, $L^2$ and $L^3$ are each independently of the others $C_1$–$C_4$-alkyl or benzyl and $An^\ominus$ is in each case one equivalent of an anion. Suitable anions include for example fluoride, chloride, bromide, iodide, mono-, di- or trichloroacetate, methanesulfonate, benzenesulfonate or 2- or 4-methylbenzenesulfonate.

Anchor radical E undergo substitutive or additive reactions with the hydroxyl or nitrogenous groups of the substrates to be treated.

The fact that the anchor radical reacts substitutively with the relevant groups in the substrates, for example with the hydroxyl groups of cellulose, means that the leaving groups or atoms (eg. fluorine or chlorine) in the anchor radical are replaced by the hydroxyl groups of the cellulose as per the following scheme:

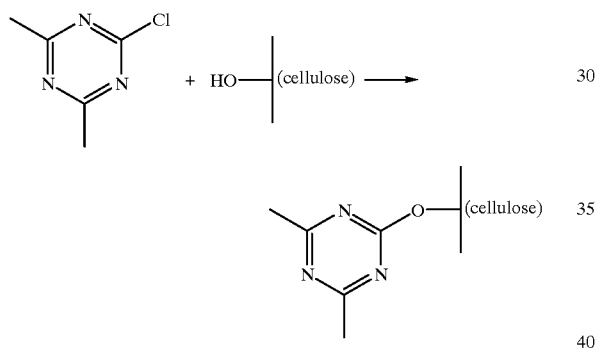

The fact that the anchor radical reacts additively with the relevant groups in the substrates, for example with the hydroxyl groups of cellulose, means that the hydroxyl groups of the cellulose are added to the anchor radical as per the following scheme:

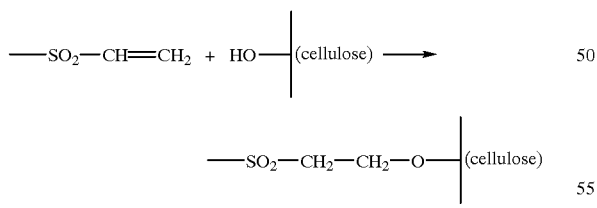

Heterocyclic anchor radicals E include for example halogen-containing radicals derived from the following basic heterocyclic species: 1,3,5-triazine, quinoxaline, phthalazine, pyrimidine or pyridazine or the 2-alkylsulfonylbenzothiazole radical.

The following are particularly suitable heterocyclic radicals:

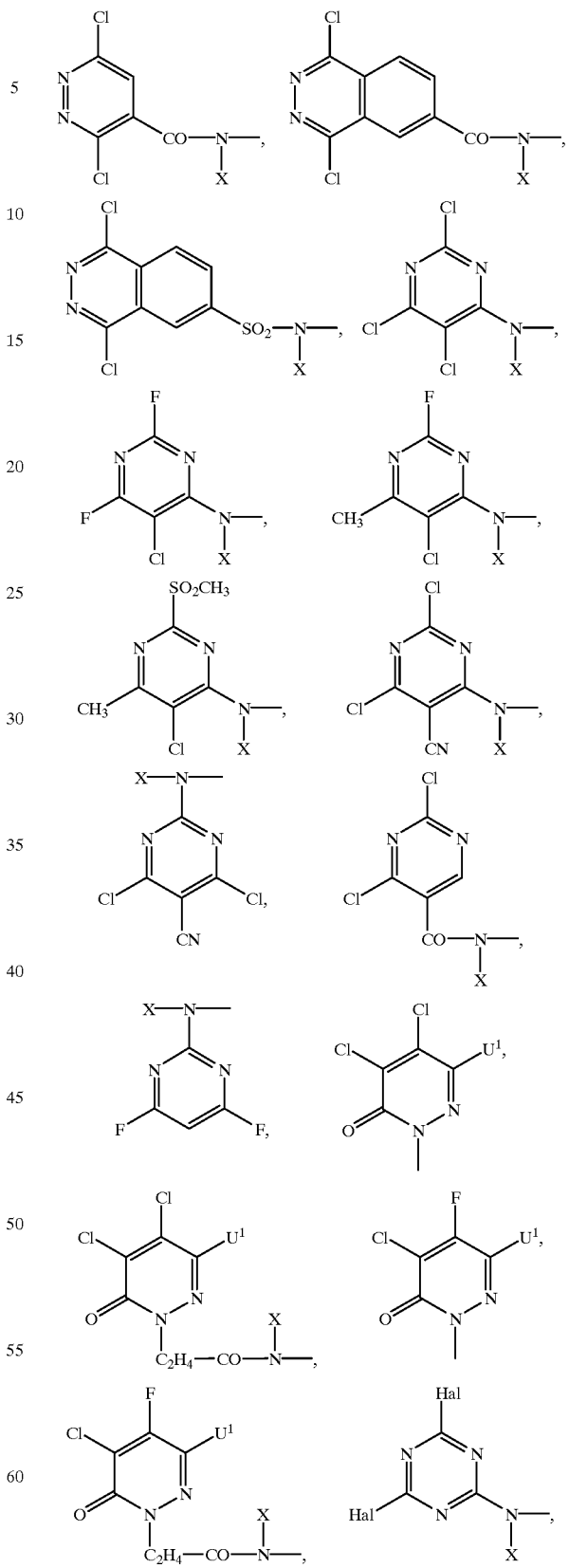

-continued

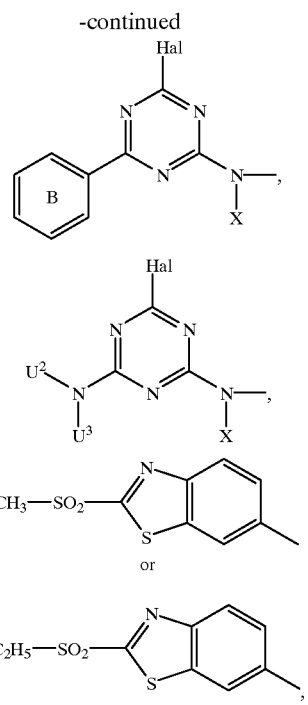

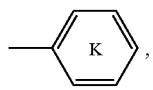

where

X is hydrogen or $C_1$-$C_4$-alkyl,

Hal is fluorine or chlorine, $U^1$ is hydrogen or nitro, and $U^2$ and $U^3$ are each independently of the other hydrogen, $C_1$-$C_6$-alkyl with or without substitution by hydroxyl, halogen, cyano, hydroxysulfonyl or a radical of the formula —$SO_2$—Y, where Y is as defined above, and with or without interruption by one or two oxygen atoms in ether function or nonadjacent imino or $C_1$-$C_4$-alkylimino groups, or $U^2$ and $U^3$ are together with the nitrogen atom joining them together pyrrolidinyl, piperidinyl, morpholinyl, piperazinyl or N-($C_1$-$C_4$-alkyl)piperazinyl, or else $U^2$ may also be a radical of the formula in which case the rings B and K may each be singly or doubly hydroxysulfonyl-substituted and/or benzofused and ring K may independently be monosubstituted or disubstituted by chlorine, nitro, $C_1$-$C_4$-alkyl, $C_1$-$C_4$-alkoxy, cyano, carboxyl, acetylamino, hydroxysulfonylmethyl or a radical of the formula $CH_2$—$SO_2$—Y, $SO_2$—Y, NH—CO—Y or $NU^2$—CO—$NU^2$—Z—$SO_2$—Y, where Y and $U^2$ are each as defined above and Z is $C_2$-$C_6$-alkylene with or without substitution by hydroxyl, chlorine, cyano, carboxyl, $C_1$-$C_4$-alkoxycarbonyl, $C_1$-$C_4$-alkanoyloxy or sulfato and with or without interruption by 1 or 2 oxygen atoms in ether function or nonadjacent imino or $C_1$-$C_4$-alkylimino groups.

Aliphatic anchor radicals E include for example acryloyl, mono-, di- or trichloroacryloyl, mono-, di- or tribromoacryloyl, —CO—CCl═CH—COOH, —CO—CH═CCl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2,3,3-trifluoro-2-chlorocyclobutylcarbonyl, 2,2,3,3-tetrafluorocyclobutylcarbonyl, 2,2,3,3-tetrafluorocyclobutylsulfonyl, 2-(2,2,3,3-tetrafluorocyclobutyl)acryloyl, 1- or 2-alkyl- or 1- or 2-arylsulfonylacryloyl, such as 1- or 2-methylsulfonylacryloyl, or a radical of the formula $SO_2$—Y, $W^1$—$SO_2$—Y, CONX—$W^2$—$SO_2$—Y or NXCONX—$W^2$—$SO_2$—Y, where X and Y are each as defined above, $W^1$ is $C_1$-$C_4$-alkylene and $W^2$ is $C_1$-$C_4$-alkylene or substituted or unsubstituted phenylene.

$W^1$ and $W^2$ are each for example $CH_2$, $(CH_2)_2$, $(CH_2)_3$, $(CH_2)_4$, $CH(CH_3)CH_2$ or $CH(CH_3)CH(CH_3)$.

$W^2$ may further be for example 1,2-, 1,3- or 1,4-phenylene.

T in the formula I is a bridge member. Suitable bridge members conform for example to the formula

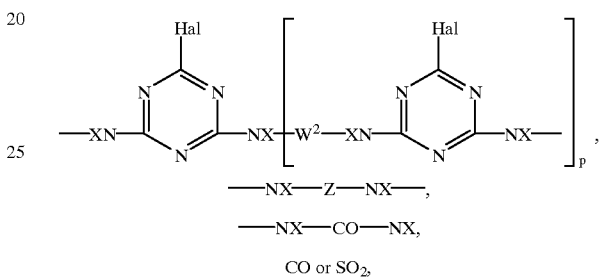

—NX—Z—NX—,

—NX—CO—NX,

CO or $SO_2$, where p is 0 or 1 and Hal, $W^2$, X and Z are each as defined above.

Particularly suitable bridge members are radicals of the formula

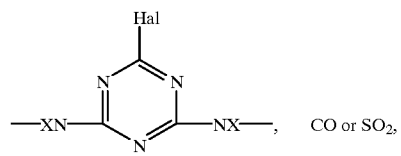, CO or $SO_2$, of which CO and $SO_2$ are preferred.

When n is 2, D preferably conforms to the formula

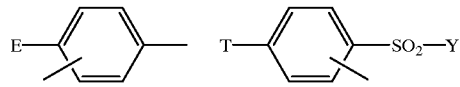

where E, Y and T are each as defined above.

Preference is given to reactive dyes of the formula I where $R^3$, $R^4$ and $R^5$ are each hydrogen.

Preference is further given to reactive dyes of the formula I where E is hydrogen, a anchor radicals of the 1,3,5-triazine series or a radical of the formula $SO_2$—Y, where Y is as defined above.

Preference is further given to reactive dyes of the formula I where T is a radical of the formula CO or $SO_2$ when n is 2.

Preference is further given to reactive dyes of the formula I where n is 1.

Preference is further given to reactive dyes of the formula I where the ring A is not benzofused.

Preference is further given to reactive dyes of the formula Ia

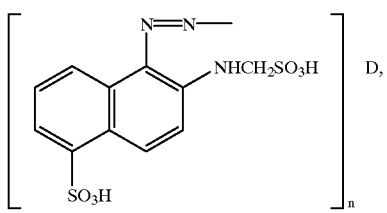

(Ia)

where n and D are each as defined above.

Preference is further given to reactive dyes of the formula Ib

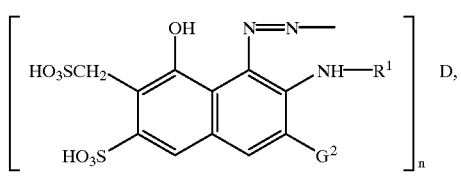

(Ib)

where n, D, $G^2$ and $R^1$ are each as defined above.

Preference is further given to reactive dyes of the formula Ic

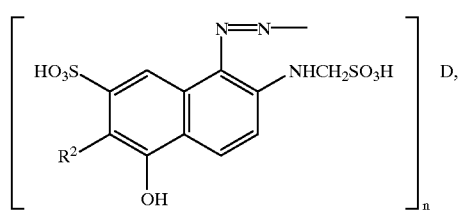

(Ic)

where n, D and $R^2$ are each as defined above.

Preference is further given to reactive dyes of the formula Id

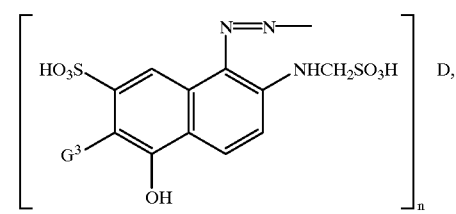

(Id)

where $G^3$ is a radical of the formula

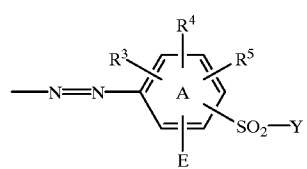

and n, D, the ring A, E, $R^3$, $R^4$, $R^5$ and Y are each as defined above.

Particular preference is given to reactive dyes of the formula I where E is hydrogen or a radical of the formula $SO_2$—Y, where Y is as defined above.

Particular preference is further given to reactive dyes of the formula I, in particular of the formulae I a–d, where the radical of the formula $SO_2$—Y is disposed ortho to the azo group.

The novel reactive dyes of the formula I are obtainable in a conventional manner.

For example, an aniline of the formula IIa or IIb

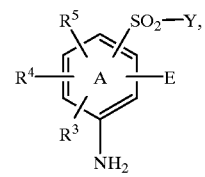

(IIa)

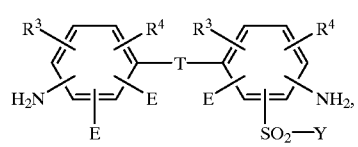

(IIb)

where the ring A, $R^3$, $R^4$, $R^5$, E, Y and T are each as defined above, can be diazotized or tetraazotized in a conventional manner and coupled with aminonaphthalene of the formula III

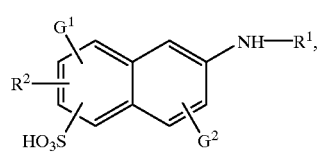

(III)

where $G^1$, $G^2$, $R^1$ and $R^2$ are each as defined above.

The anilines of the formula IIb are obtainable in a conventional manner, for example as described in prior patent application DE-A-195 08 311.

The present invention further provides naphthylamines of the formula III

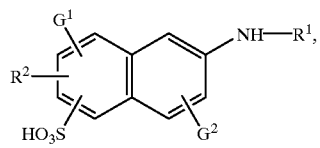

(III)

where $G^1$ is hydrogen or hydroxyl, $G^2$ is hydrogen or hydroxysulfonyl, $R^1$ is hydrogen or hydroxysulfonylmethyl, and $R^2$ is hydrogen or hydroxysulfonylmethyl with the proviso that at least one hydroxysulfonylmethyl group shall be present in the molecule, and that naphthylamines of the formula

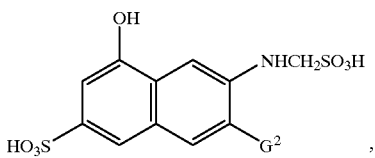

where G² is as defined above, shall be excluded.

Preference is given to naphthylamines of the formulae IIIa to IIIc

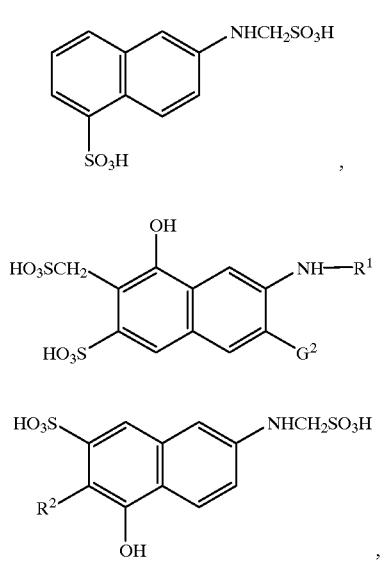

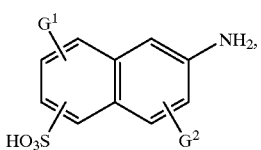

where G², R¹ and R² are each as defined above.

The novel naphthylamines of the formula III are obtainable in a conventional manner.

For example, a naphthylene derivative of the formula IV

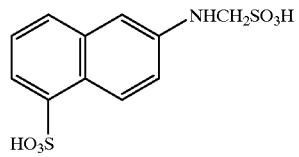

where G¹ and G² are each as defined above, can be reacted in a basic medium with the addition product of an alkali metal bisulfite with formaldehyde, eg. formaldehyde sodium bisulfite of the formula $HOCH_2SO_3Na$.

By partial hydrolysis in the alkaline region the hydroxysulfonylamino group can also be converted back into the free amino group.

The novel reactive dyes of the formula I are advantageously useful for dyeing or printing hydroxyl-containing or nitrogenous organic substrates. Such substrates include for example leather or fiber material predominantly comprising natural or synthetic polyamides or natural or regenerated cellulose. The novel dyes are preferably useful for dyeing and printing textile material based on wool and in particular on cotton. The dyeings obtained have red shades.

Cellulose-based substrates in particular are dyed with a very high yield of fixation in strong dyeings having very good lightfastness and also excellent wetfastness properties, such as wash, chlorine bleach, peroxide bleach, alkali, seawater or perspiration fastness properties.

The Examples which follow illustrate the invention.

EXAMPLE 1 a) 149 g (0.5 mol) of 2-aminonaphthalene-5-sulfonic acid were suspended in 750 ml of water and dissolved by adding sodium hydroxide solution. 106 g (0.75 mol) of formaldehyde sodium bisulfite were added at pH 6.5 a little at a time and the mixture was stirred at 60° C. for 4 h. 200 g of sodium chloride were added to precipitate the product of the formula

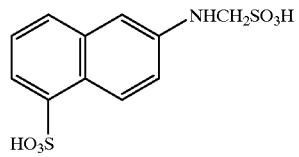

to obtain 449 g (0.4 mol) of a moist paste.

b) 15 g (0.05 mol) of 4-(2-sulfatoethylsulfonyl)aniline were suspended in 200 ml of ice-water, admixed with 15 ml of 10N hydrochloric acid and diazotized at 0–5° C. by the dropwise addition of 15 ml of 23% strength by weight aqueous sodium nitrite solution with stirring. After stirring at 0–5° C. for 2 hours, the small excess of nitrous acid was destroyed with sulfamic acid. To this solution were added 56 g (0.05 mol) of the compound described under a), and the reaction solution was held at a pH of from 2.5 to 3 with sodium acetate. After the reaction had ended, the reaction mixture was warmed to room temperature, and the pH was adjusted to 5–5.5 with sodium carbonate. 300 ml of methanol and 2 l of acetone were added to obtain 27 g (0.044 mol) of the scarlet dye of the formula

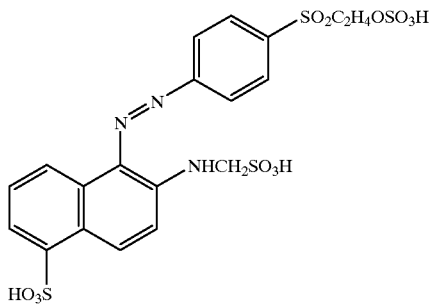

$\lambda_{max}$ (water): 483 nm.

The following dyes were obtained in a similar manner:

EXAMPLE 2

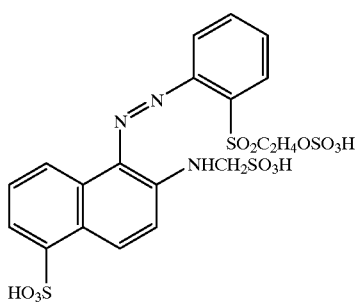

λ$_{max}$ (water): 495 nm

EXAMPLE 3

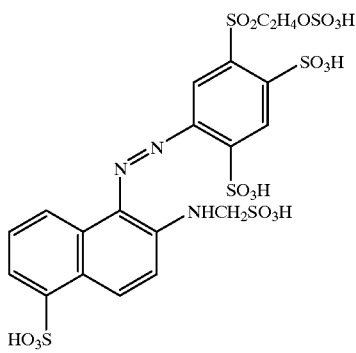

λ$_{max}$ (water): 514 nm

EXAMPLE 4

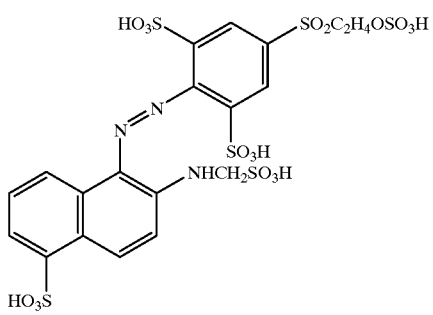

λ$_{max}$ (water): 475 nm

EXAMPLE 5

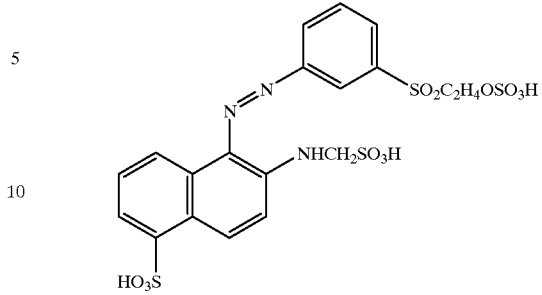

λ$_{max}$ (water): 514 nm.

EXAMPLE 6 a) 207 g (0.5 mol) of 2-amino-8-hydroxynaphthalene-3, 6-disulfonic acid were suspended in 750 ml of water and dissolved by adding sodium hydroxide solution. 176.5 g (1.25 mol) of formaldehyde sodium bisulfite were added at pH 8.5 a little at a time and the mixture was stirred at 60° C. for 20 h. 350 g of potassium chloride were added to precipitate the product of the formula

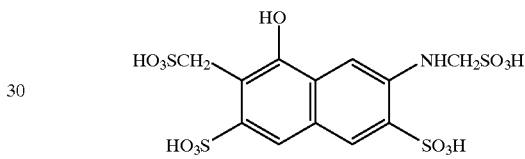

to obtain 523 g of a moist paste.

b) 523 g of the compound prepared under a) were suspended in 800 ml of water and admixed with 75 ml (1.35 mol) of aqueous sodium hydroxide solution and stirred at 80° C. for 7 h. After the reaction had ended, a pH of 3 was set with dilute hydrochloric acid and the dye was salted out with 300 g of potassium chloride to obtain 182.5 g (0.35 mol) of a beige solid of the formula

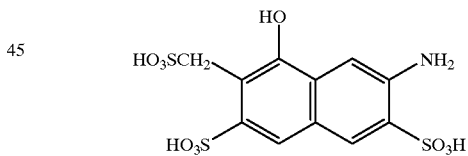

c) 25 g (0.05 mol) of 3-(2-sulfatoethylsulfonyl)aniline-4, 6-disulfonic acid were suspended in 200 ml of ice-water, admixed with 15 ml of 10N hydrochloric acid and diazotized at 0–5° C. by the dropwise addition of 15 ml of 23% strength by weight aqueous sodium nitrite solution with stirring. After stirring at from 0 to 5° C. for 3 hours, the small excess of nitrous acid was destroyed with sulfamic acid. To this solution were added 26 g (0.05 mol) of the compound described under b), and the reaction solution was held at a pH of from 2.5 to 3 with sodium acetate. After the reaction had ended, the reaction mixture was warmed to room temperature, and the pH was adjusted to 5–5.5 with sodium bicarbonate. Precipitation with a methanol/acetone mixture yielded 38.3 g (0.044 mol) of a reddish violet dye of the formula

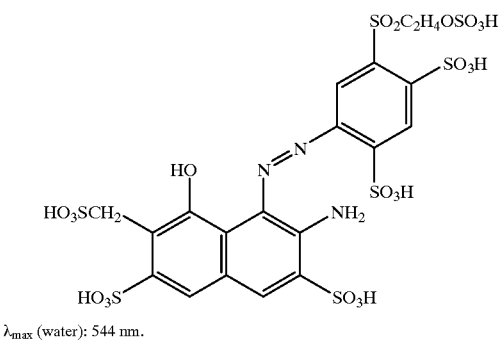

λ<sub>max</sub> (water): 544 nm.

The following dyes were obtained in a similar manner:

EXAMPLE 7

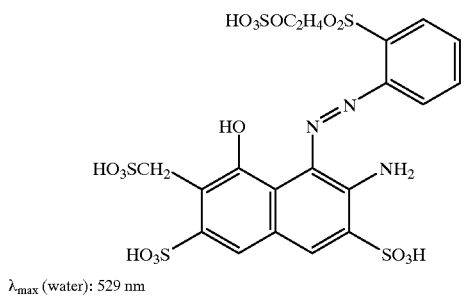

λ<sub>max</sub> (water): 529 nm

EXAMPLE 8

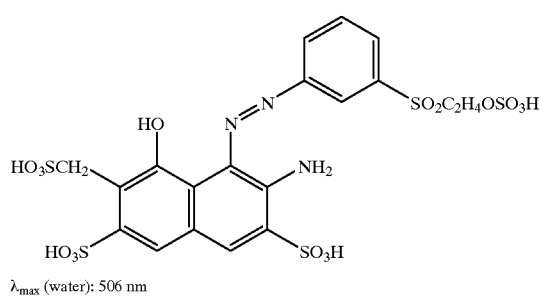

λ<sub>max</sub> (water): 506 nm

EXAMPLE 9

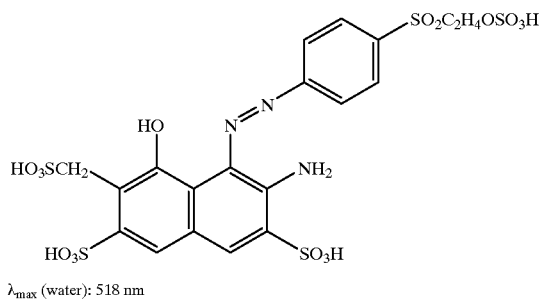

λ<sub>max</sub> (water): 518 nm

EXAMPLE 10 a) 129 g (0.5 mol) of 2-amino-8-hydroxynaphthalene-6-sulfonic acid were suspended in 750 ml of water and dissolved with sodium hydroxide solution. 176.3 g (1.25 mol) of formaldehyde sodium bisulfite were added a little at a time at pH 8–8.5 and the mixture was stirred at 60° C. for 9 h. After the reaction had ended, the product was precipitated with 300 g of sodium chloride to obtain 447 g (0.41 mol) of a beige solid of the formula

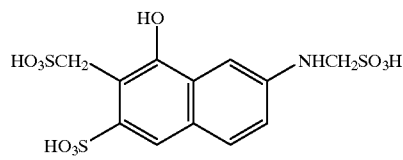

b) 15 g (0.05 mol) of 2-(2-sulfatoethylsulfonyl)aniline were suspended in 200 ml of ice-water, admixed with 20 ml of 10N hydrochloric acid and diazotized at 0–5° C. by the dropwise addition of 15 ml of 23% strength by weight aqueous sodium nitrite solution with stirring. After stirring at 0–5° C. for 2 hours, the small excess of nitrous acid was destroyed with sulfamic acid. To this solution were added 55 g (0.05 mol) of the compound described under a), and the reaction solution was held at a pH of from 2.5 to 3 with sodium acetate. After the reaction had ended, the reaction mixture was warmed to room temperature, and the pH was adjusted to 5–5.5 with sodium bicarbonate. Precipitating with the methanol/acetone mixture yielded 37.9 g (0.047 mol) of a reddish violet dye of the formula

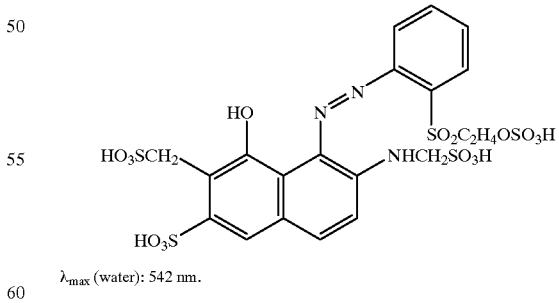

λ<sub>max</sub> (water): 542 nm.

The following dyes were obtained in a similar manner:

EXAMPLE 11

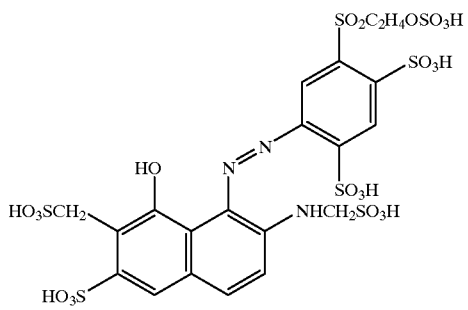

λ$_{max}$ (water): 554 nm

EXAMPLE 12

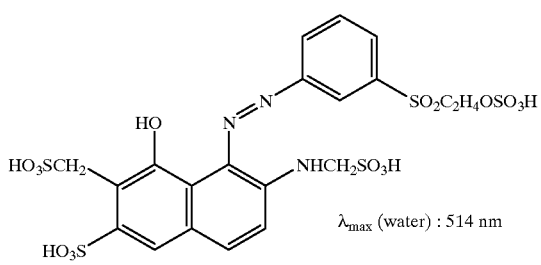

λ$_{max}$ (water) : 514 nm

EXAMPLE 13

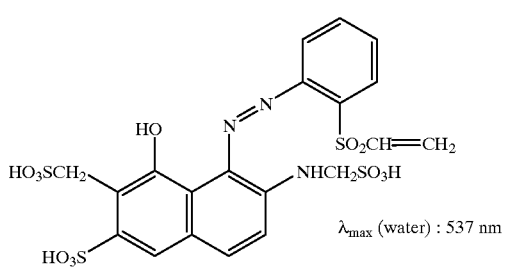

λ$_{max}$ (water) : 537 nm

EXAMPLE 14

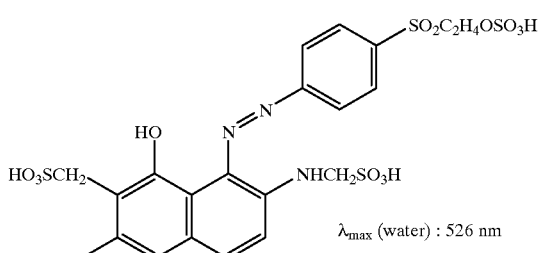

λ$_{max}$ (water) : 526 nm

EXAMPLE 15 a) 129 g (0.5 mol) of 2-amino-8-hydroxynaphthalene-6-sulfonic acid were suspended in 750 ml of water and dissolved with sodium hydroxide solution. 176.3 g (1.25 mol) of formaldehyde sodium bisulfite were added a little at a time at pH 8–8.5 and the mixture was stirred at 60° C. for 9 h. After the reaction had ended, 137.5 ml (2.5 mol) of 50% strength by weight sodium hydroxide solution were added and the mixture was heated at 90° C. for 1.5 h. Thereafter it was adjusted to pH 5 with dilute hydrochloric acid, and the precipitate was filtered off. The paste was suspended in 800 ml of water and admixed with 100 ml of saturated aqueous sodium chloride solution to obtain 208 g (0.358 mol) of a moist paste of the formula

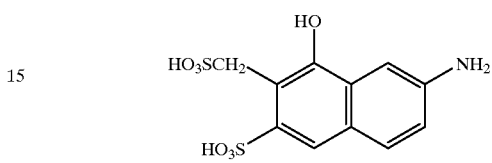

b) 13.5 g (0.045 mol) of 2-(2-sulfatoethylsulfonyl)aniline were suspended in 200 ml of ice-water, admixed with 20 ml of 10N hydrochloric acid and diazotized at 0–5° C. by the dropwise addition of 13.5 ml of 23% strength by weight aqueous sodium nitrite solution with stirring. After stirring at 0–5° C. for 2 hours, the small excess of nitrous acid was destroyed with sulfamic acid. To this solution were added 31 g (0.045 mol) of the compound prepared under a), and the reaction solution was held at a pH of from 3.5 to 4 with sodium acetate. After the reaction had ended, the reaction mixture was warmed to room temperature, and the pH was adjusted to 5–5.5 with sodium bicarbonate. The product was precipitated by adding 100 g of sodium chloride to obtain 34 g (0.041 mol) of a red dye of the formula

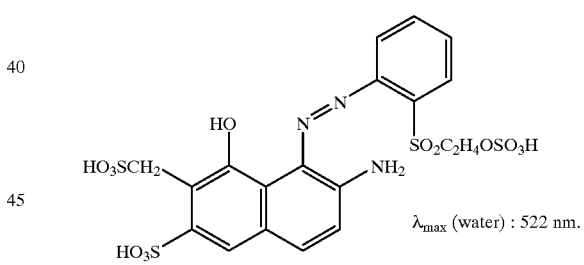

λ$_{max}$ (water) : 522 nm.

The following dyes were obtained in a similar manner:

EXAMPLE 16

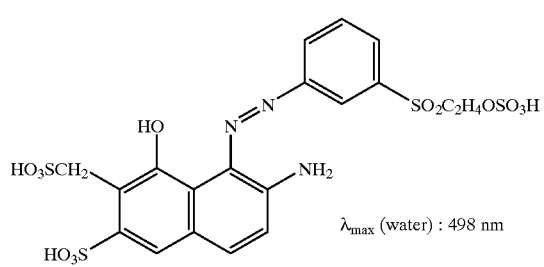

λ$_{max}$ (water) : 498 nm

EXAMPLE 17

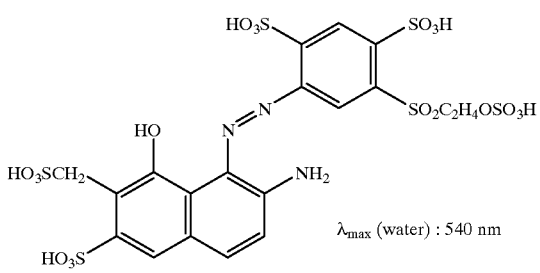

λ_max (water) : 540 nm

EXAMPLE 18

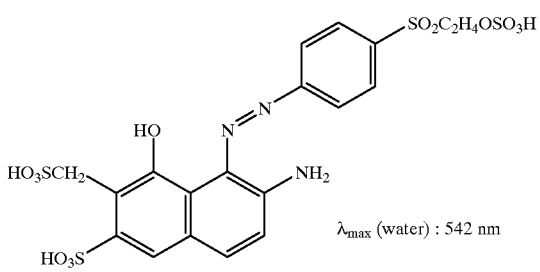

λ_max (water) : 542 nm

EXAMPLE 19 a) 386 g (1.5 mol) of 2-amino-5-hydroxynaphthalene-7-sulfonic acid were suspended in 2250 ml of water and dissolved with sodium hydroxide solution. 318 g (2.25 mol) of formaldehyde sodium bisulfite were added at pH 5 and the mixture was stirred at 60° C. for 4 h. After the reaction had ended, the resulting product of the formula

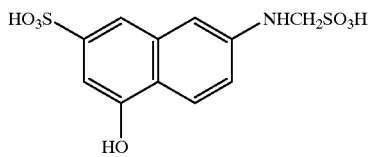

was not isolated but used as a coupling component in solution.

b) 14.5 g (0.05 mol) of 3-(2-sulfatoethylsulfonyl)aniline were suspended in 200 ml of ice-water, admixed with 20 ml of 10N hydrochloric acid and diazotized at 0–5° C. by dropwise addition of 15 ml of 23% strength by weight aqueous sodium nitrite solution with stirring. After stirring at 0–5° C. for 3 hours, the small excess of nitrous acid was destroyed with sulfamic acid.

106 ml (0.053 mol) of the solution described under a) were admixed with ice and adjusted to pH 3 with dilute hydrochloric acid. The diazonium salt solution was added dropwise to this solution while a pH of 2.5–3 was maintained with sodium acetate. After the reaction had ended, the mixture was warmed to room temperature and the pH was adjusted to 5–5.5 with sodium bicarbonate. The dye was precipitated by adding 150 g of potassium chloride and 50 g of sodium chloride. Filtration left 37.5 g (0.048 mol) of a scarlet dye of the formula

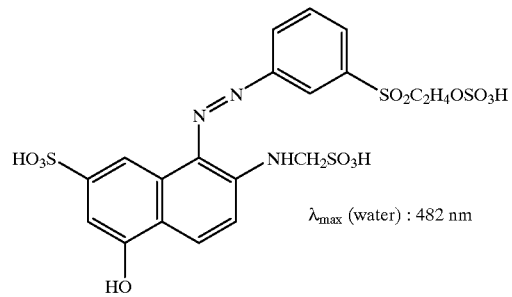

λ_max (water) : 482 nm

The following dyes were obtained in a similar manner:

EXAMPLE 20

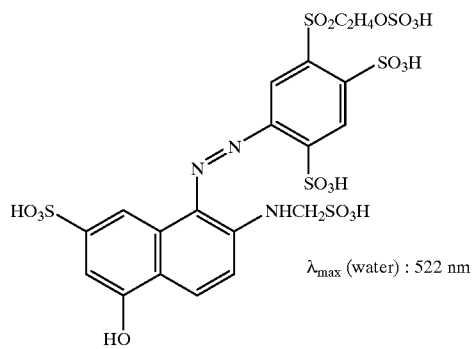

λ_max (water) : 522 nm

EXAMPLE 21

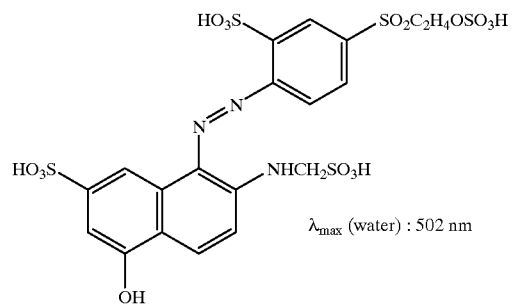

λ_max (water) : 502 nm

EXAMPLE 22 a) 2 l (1.0 mol) of the solution described in Example 19a) were adjusted to pH 8.5 with sodium hydroxide solution and heated to 60° C. At that temperature, 70.5 g (0.05 mol) of formaldehyde sodium bisulfite were added and the mixture was stirred at 60° C. for 2 hours. After the reaction had ended, the resulting compound of the formula

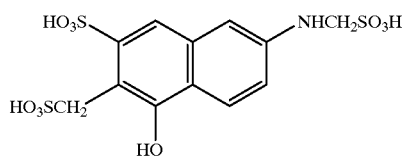

was not isolated but used in solution as coupling component.

b) 14.5 g (0.05 mol) of 3-(2-sulfatoethylsulfonyl)aniline were suspended in 200 ml of ice-water, admixed with 20 ml of 10N hydrochloric acid and diazotized at 0–5° C. by dropwise addition of 15 ml of 23% strength by weight aqueous sodium nitrite solution with stirring. After stirring at 0–5° C. for 3 hours, the small excess of nitrous acid was destroyed with sulfamic acid.

112 ml (0.053 mol) of the solution described under a) were admixed with ice and adjusted to pH 3 with dilute hydrochloric acid. The diazonium salt solution was added dropwise to this solution while a pH of 2.5–3 was maintained with sodium acetate. After the reaction had ended, the mixture was warmed to room temperature and the pH was adjusted to 5–5.5 with sodium bicarbonate. The dye was precipitated by adding 200 g of sodium chloride. Filtration left 47.8 g (0.045 mol) of a scarlet dye of the formula

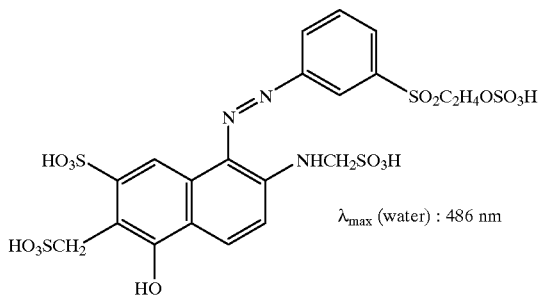

$\lambda_{max}$ (water) : 486 nm

The following dyes were obtained in a similar manner:

EXAMPLE 23

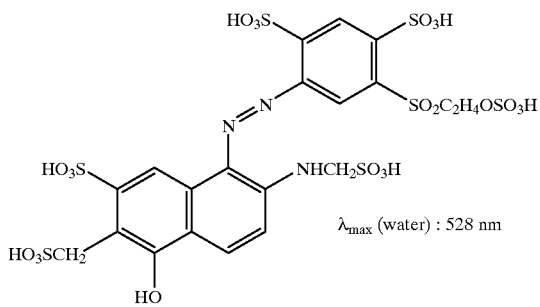

$\lambda_{max}$ (water) : 528 nm

EXAMPLE 24

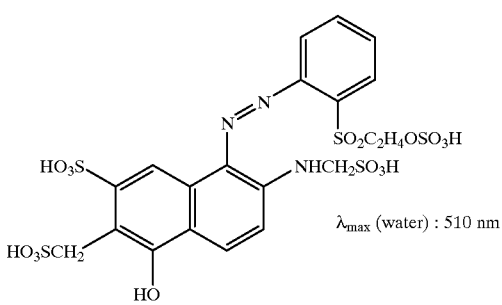

$\lambda_{max}$ (water) : 510 nm

EXAMPLE 25 a) 1.05 l (0.5 mol) of the solution described in Example 22 a) were heated to 60° C. and admixed a little at a time at that reaction temperature with a total of 137.5 ml (2.5 mol) of 50% strength by weight sodium hydroxide solution. After the reaction had ended, the pH was adjusted to 5 with dilute hydrochloric acid and 200 g of sodium chloride were added to isolate 497 g (0.33 mol) of moist paste of the formula

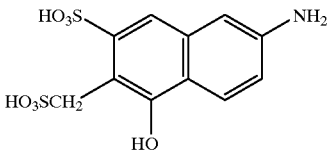

b) 14.5 g (0.05 mol) of 3-(2-sulfatoethylsulfonyl)aniline were suspended in 200 ml of ice-water, admixed with 20 ml of 10N hydrochloric acid and diazotized at 0–5° C. by the dropwise addition of 15 ml of 23% strength by weight aqueous sodium nitrite solution with stirring. After stirring at 0–5° C. for 2 hours, the small excess of nitrous acid was destroyed with sulfamic acid. To this solution were added 74 g (0.05 mol) of the compound prepared under a) and the reaction solution was held at pH 3.5–4 with sodium acetate. After the reaction had ended, the mixture was warmed to room temperature and the pH was adjusted to 5–5.5 with sodium bicarbonate. Precipitating with a methanol/ethanol mixture yielded 35.1 g (0.042 mol) of the dye of the formula

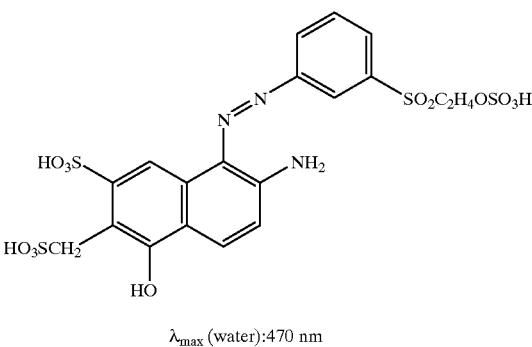

$\lambda_{max}$ (water):470 nm

The following dye was obtained in a similar manner:

EXAMPLE 26

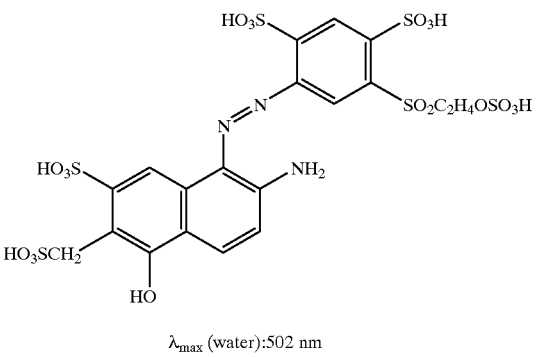

$\lambda_{max}$ (water):502 nm

EXAMPLE 27

35.3 g (0.075 mol) of 3-(2-sulfatoethylsulfonyl)aniline-4,6-disulfonic acid were suspended in 300 ml of ice-water, admixed with 30 ml of 10N hydrochloric acid and diazotized at 0–5° C. by dropwise addition of 22.5 ml of 23% strength by weight aqueous sodium nitrite solution with stirring. After stirring at 0–5° C. for 2 hours, the small excess of nitrous acid was destroyed with sulfamic acid. 70 ml (0.035 mol) of the solution described in Example 19 a) were admixed with ice and adjusted to pH 3 with dilute hydrochloric acid. Half the diazonium salt solution was added dropwise to this solution while the pH was held within the range from 2.5 to 3 with sodium acetate. After the coupling in the ortho position to the amino group was complete, the pH was raised to 5–5.5 and the rest of the diazonium salt solution was added dropwise. Precipitating with methanol/ethanol mixture yielded 50.3 g (0.034 mol) of a scarlet dye of the formula

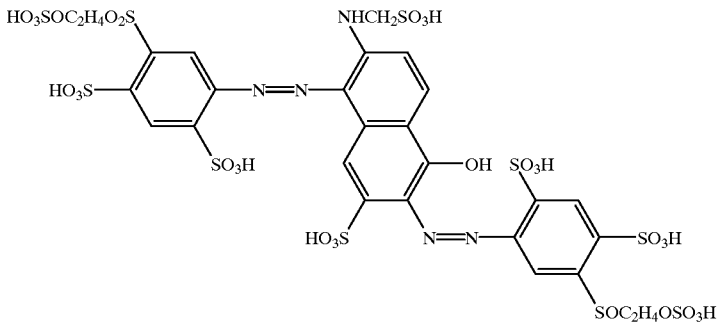

$\lambda_{max}$ (water):490 nm

The following dyes were obtained in a similar manner:

EXAMPLE 28

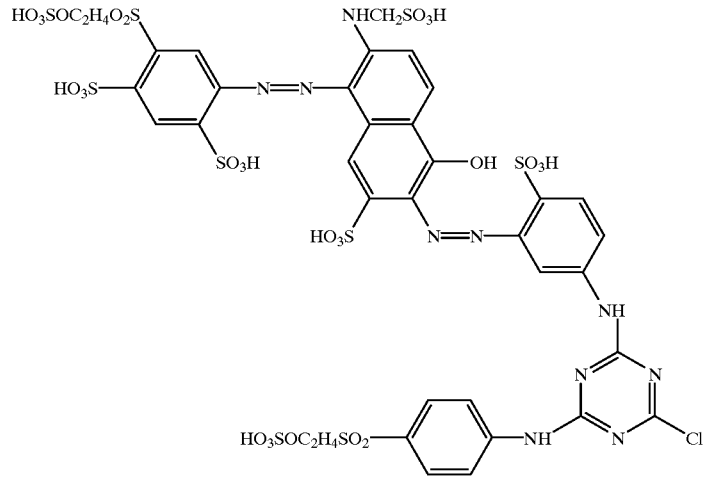

$\lambda_{max}$ (water):510 nm

EXAMPLE 29
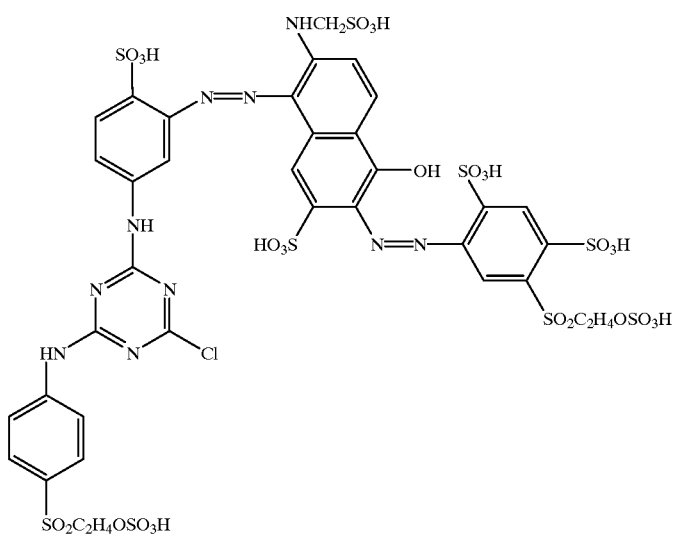
λ$_{max}$ (water): 494 nm
EXAMPLE 30
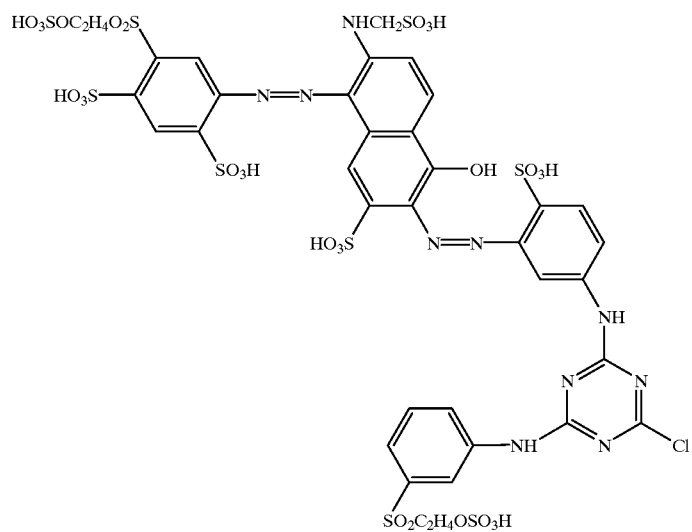
λ$_{max}$ (water): 506 nm

EXAMPLE 31
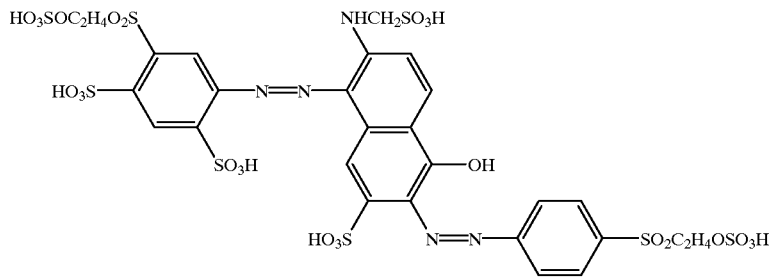
λ_max (water): 500 nm
EXAMPLE 32
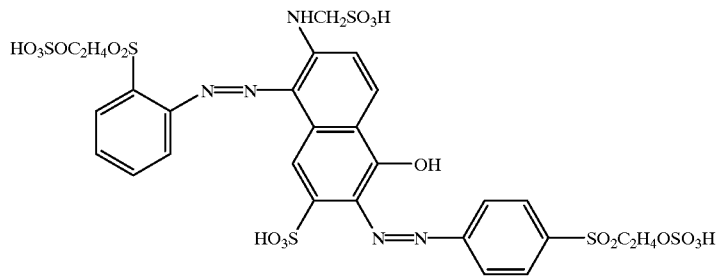
λ_max (water): 495 nm
EXAMPLE 33
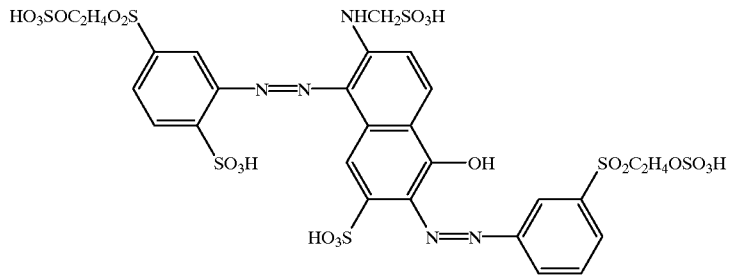
λ_max (water): 492 nm

EXAMPLE 34
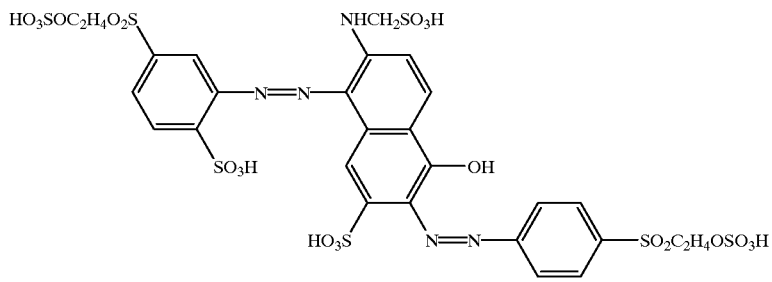
$\lambda_{max}$ (water): 496 nm
EXAMPLE 35
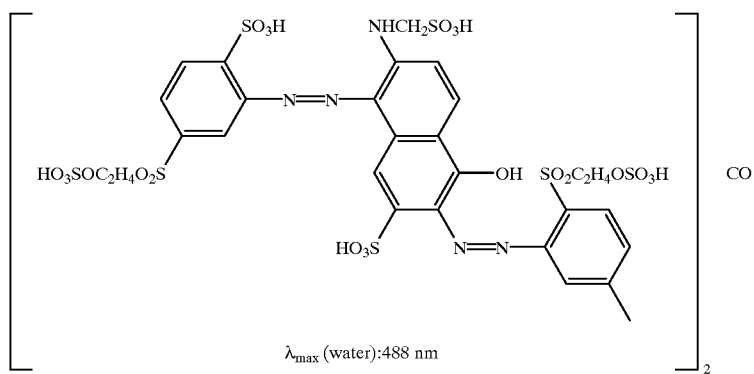
$\lambda_{max}$ (water): 488 nm
EXAMPLE 36
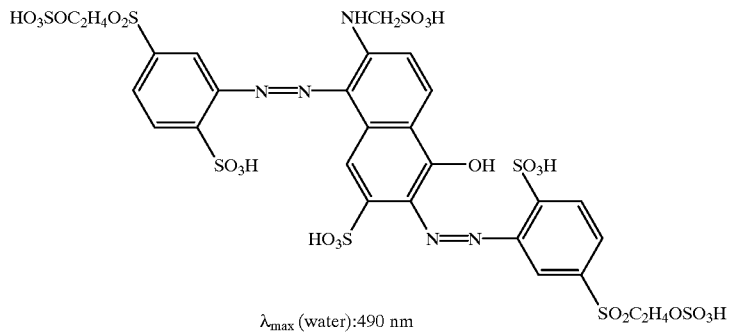
$\lambda_{max}$ (water): 490 nm
We claim:
1. A reactive dye of the formula I
$$\left[ \begin{array}{c} \text{structure with } G^1, G^2, G^3, R^1, R^2, HO_3S, NH-R^1, N=N-D \end{array} \right]_n$$ (I)
where
n is 1 or 2,
$G^1$ is hydrogen or hydroxyl,
$G^2$ is hydrogen or hydroxysulfonyl, $G^3$ is hydrogen or a radical of the formula

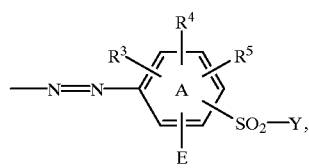

$R^1$ is hydrogen or hydroxysulfonylmethyl,
$R^2$ is hydrogen or hydroxysulfonylmethyl, and
D is, when n is 1, a radical of the formula

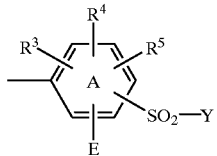

or, when n is 2, a radical of the formula

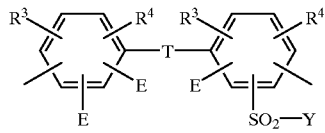

where the ring A may be benzofused, $R^3$, $R^4$ and $R^5$ are each independently of the others hydrogen, $C_1$–$C_4$-alkyl, $C_1$–$C_4$-alkoxy, halogen or hydroxysulfonyl, E is hydrogen, a heterocyclic anchor radical or a anchor radical of the aliphatic series, Y is vinyl or a radical of the formula $C_2H_4$—Q, where Q is an alkali-detachable group, and T is a bridge member,
with the proviso that at least one hydroxysulfonylmethyl group shall be present in the molecule and that dyes of the formula

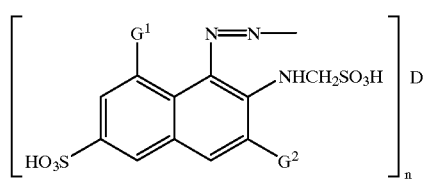

where n, $G^7$ and $G^2$ are each as defined above, shall be excluded.

2. The reactive dye as claimed in claim 1 which conform to the formula Ia

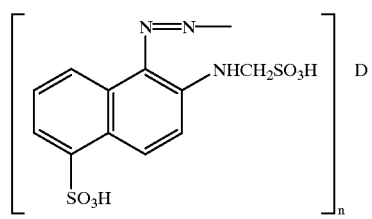

where n and D are each as defined in claim 1.

3. The reactive dye as claimed in claim 1 which conform to the formula Ib

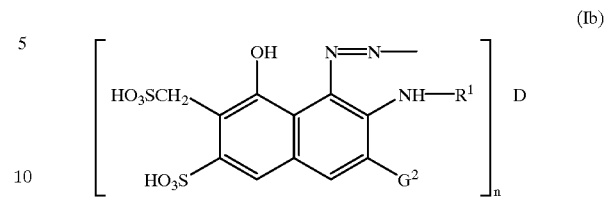

where n, D, $G^2$ and $R^1$ are each as defined in claim 1.

4. The reactive dye as claimed in claim 1 which conform to the fomula Ic

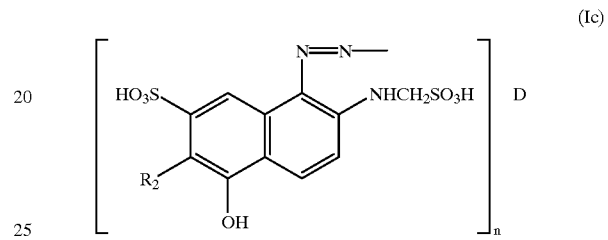

where n, D and $R^2$ are each as defined in claim 1.

5. The reactive dye as claimed in claim 1 which conform to the formula Id

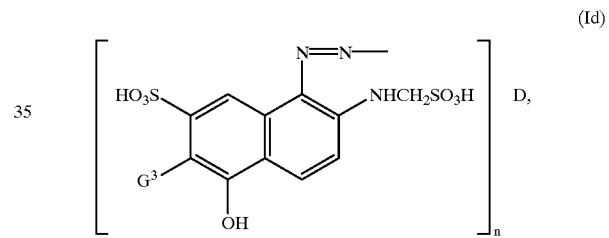

where $G^3$ is a radical of the formula

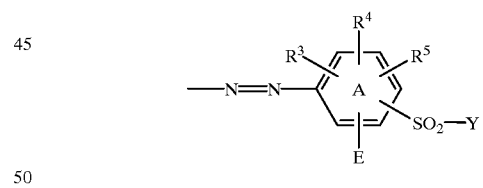

and n, D, the ring A, E, $R^3$, $R^4$, $R^5$, $G^2$ and Y are each as defined in claim 1.

6. The reactive dye as claimed in claim 1, wherein $R^3$, $R^4$ and $R^5$ are each hydrogen.

7. The reactive dye as claimed in claim 1, wherein T is a radical of the formula CO or $SO_2$ when n is 2.

8. The reactive dye as claimed in claim 1, wherein n is 1.

9. The reactive dye as claimed in claim 1, wherein E is hydrogen or a radical of the formula $SO_2$—Y, where Y is as defined in claim 1.

10. The reactive dye as claimed in claim 1, wherein the radical of the formula $SO_2$—Y is ortho to the azo group.

11. A method for dyeing or printing a hydroxyl-containing or nitrogenous organic substrate comprising applying the reactive dye of claim 1 to said substrate.

* * * * *